(12) United States Patent
Jussel (10) Patent No.: US 9,759,487 B2
(45) Date of Patent: Sep. 12, 2017

(54) DENTAL FIRING OR PRESS FURNACE

(71) Applicant: Ivoclar Vivadent AG, Schaan (LI)

(72) Inventor: Rudolf Jussel, Feldkirch-Gisingen (AT)

(73) Assignee: Ivoclar Vivadent AG, Schaan (LI)

( * ) Notice: Subject to any disclaimer, the term of this patent is extended or adjusted under 35 U.S.C. 154(b) by 459 days.

(21) Appl. No.: 14/260,445

(22) Filed: Apr. 24, 2014

(65) Prior Publication Data

US 2014/0231405 A1    Aug. 21, 2014

Related U.S. Application Data

(63) Continuation-in-part of application No. 13/406,698, filed on Feb. 28, 2012, now Pat. No. 8,742,298.

(30) Foreign Application Priority Data

Mar. 2, 2011   (EP) ..................................... 11156684

(51) Int. Cl.
| | |
|---|---|
| *F27B 17/00* | (2006.01) |
| *A61C 13/20* | (2006.01) |
| *F27B 5/10* | (2006.01) |
| *F27B 17/02* | (2006.01) |

(52) U.S. Cl.
CPC .............. *F27B 5/10* (2013.01); *F27B 17/025* (2013.01); *A61C 13/20* (2013.01)

(58) Field of Classification Search
CPC ... A61C 13/20; A61C 13/0006; A61C 13/083; F27B 17/00; F27B 17/025
USPC ....... 219/392, 390, 399, 407, 521, 530, 540; 432/241, 253, 247, 258; 373/104, 111, 373/112, 119, 157
See application file for complete search history.

(56) References Cited

U.S. PATENT DOCUMENTS

| | | | |
|---|---|---|---|
| 1,534,592 A | | 4/1925 | Houck |
| 3,463,470 A | | 8/1969 | Green et al. |
| 3,860,738 A | | 1/1975 | Hintenberger |
| 4,332,553 A | | 6/1982 | Earle et al. |
| 4,671,770 A | | 6/1987 | Bell et al. |
| 4,828,490 A | | 5/1989 | Indig |
| 4,912,302 A | | 3/1990 | Kobayashi et al. |
| 4,969,818 A | * | 11/1990 | Ueda ....................... F27D 3/123 414/154 |
| 5,115,118 A | | 5/1992 | Harada et al. |
| 5,313,048 A | | 5/1994 | Berg et al. |
| 5,432,319 A | | 7/1995 | Indig |
| 5,685,360 A | | 11/1997 | Bizzio |

(Continued)

FOREIGN PATENT DOCUMENTS

| | | |
|---|---|---|
| DE | 853793 C | 10/1952 |
| DE | 860989 C | 12/1952 |

(Continued)

*Primary Examiner* — Michael Laflame, Jr.
(74) *Attorney, Agent, or Firm* — Ann M. Knab; Thad McMurray (57) ABSTRACT

The invention relates to a dental firing or press furnace (10) that enables the production of at least one dental restoration part (62). The dental firing or press furnace is provided with a firing space (12) that is heatable with the aid of a heating device (22), preferably, a resistance heating device. A heat-conducting element (50) having a specific thermal conductivity of at least 100 W/mK is arranged on the floor of the firing space (12).

24 Claims, 6 Drawing Sheets

(56) References Cited

U.S. PATENT DOCUMENTS

| | | | | |
|---|---|---|---|---|
| 5,879,128 A | * | 3/1999 | Tietz | H01L 21/68742 414/757 |
| 6,252,202 B1 | | 6/2001 | Zychek | |
| 6,384,382 B2 | * | 5/2002 | Rohner | 219/390 |
| 6,485,849 B2 | * | 11/2002 | Petticrew | A61C 13/20 106/35 |
| 6,869,280 B2 | | 3/2005 | Flieschfresser | |
| 7,198,618 B2 | * | 4/2007 | Ferguson | A61B 5/14 604/192 |
| 7,796,674 B2 | * | 9/2010 | Keough | F27B 14/063 373/142 |
| 8,232,506 B2 | | 7/2012 | Jussel | |
| 8,487,220 B2 | | 7/2013 | Serrago et al. | |
| 8,837,924 B2 | * | 9/2014 | Tsunekawa | H01L 21/67109 118/724 |
| 2002/0043526 A1 | * | 4/2002 | Blanter | H01L 21/67103 219/390 |
| 2006/0151117 A1 | * | 7/2006 | Kasanami | H01J 37/32082 156/345.52 |
| 2007/0082307 A1 | | 4/2007 | Zubler | |
| 2008/0006617 A1 | * | 1/2008 | Harris | F27B 17/0025 219/390 |
| 2008/0096148 A1 | | 4/2008 | Jussel | |
| 2008/0199823 A1 | * | 8/2008 | Miller | F27B 17/025 432/258 |
| 2008/0237211 A1 | | 10/2008 | Jussel | |
| 2009/0226855 A1 | | 9/2009 | Rohner et al. | |
| 2010/0025395 A1 | | 2/2010 | Laubersheimer et al. | |
| 2010/0047731 A1 | | 2/2010 | Zubler | |
| 2011/0006450 A1 | * | 1/2011 | Stephan | A61C 13/203 264/16 |
| 2011/0114626 A1 | | 5/2011 | Serrago et al. | |
| 2011/0177266 A1 | | 7/2011 | Miller | |
| 2012/0012577 A1 | | 1/2012 | Jussel et al. | |
| 2012/0037610 A1 | * | 2/2012 | Yoo | F27B 5/06 219/420 |
| 2012/0080425 A1 | | 4/2012 | Jussel et al. | |
| 2012/0118875 A1 | | 5/2012 | Jussel et al. | |
| 2013/0149186 A1 | | 6/2013 | Hachenberg et al. | |

FOREIGN PATENT DOCUMENTS

| | | |
|---|---|---|
| DE | 871817 C | 3/1953 |
| DE | 4433159 C1 | 1/1996 |
| JP | H08322857 A | 12/1996 |
| JP | 2007247929 A | 9/2007 |
| KR | 101250626 B1 * | 8/2010 |

* cited by examiner

DENTAL FIRING OR PRESS FURNACE

CROSS-REFERENCE TO RELATED APPLICATIONS

This application is a continuation-in-part of U.S. application Ser. No. 13/406,698, filed Feb. 28, 2012, which claims the benefit of EP 11156684.0 filed Mar. 2, 2011, all of which are hereby incorporated by reference in their entirety.

TECHNICAL FIELD

The invention relates to a dental firing or press furnace and a method for operating a dental firing or press furnace.

BACKGROUND

Firing and press furnaces for dental restoration parts are used for subjecting the dental restorations that mostly consist of glass ceramics, to a heat treatment in order to achieve a condition of the dental restoration part that is ready for the intended use. Temperatures of up to 1200° C. are required for the heat treatment in firing and press furnaces.

The quality of the produced dental restoration part to a large extent depends on the temperature profile and the temperature distribution in the dental furnace during the firing and/or pressing operation of the dental ceramic part. If the temperature gradients during the firing- or pressing operation in the dental restoration part during the heat treatment get too large, the quality of the product produced drops. In some cases this may even lead to an erroneous result, which in turn means that the dental technician's work of several hours invested before is lost. Moreover, the existing temperature gradients in a dental furnace restrict the dental technician's possibilities and/or reduce the robustness of the process.

The respective selection and the adjustment of the optimal parameters, but also the insertion of the dental restoration part into the firing furnace or the press furnace, i.e. for example the kind of firing tray or the position of the dental objects thereon during the heat treatment process, or the object positions in a press muffle regularly are up to the choice of the dental technician and strongly depend on his experience. Basically, the temperature gradients in the dental firing spaces mentioned before, in particular with short and quick thermal treatment processes, result in many conflicting situations that are difficult to solve. This is even more the case if multi-unit bridges etc. or a plurality of small dental restorations together are subjected to a heat treatment at the same time.

In particular in press muffles it is predefined for the dental technician via a sprue guide for mounting the wax parts in a press muffle, how far to the edge and how far into the center the objects are sprued. This limitation reduces the possibilities and also the number of units that can simultaneously be pressed, or the process times must be extended in general and clearly.

Further it has been proposed according to DE 199 05 666 A1 and corresponding U.S. Pat. No. 6,252,202, which is hereby incorporated by reference, to provide a lower heating element in addition to a lateral heating element in order to avoid cold surfaces in the firing space and in order to provide uniform heating in the entire heating chamber. With the aid of quartz covers a further homogenization of the radiation of heat and simultaneously some protection is to be achieved. A lower heating element of this kind, however, requires serious additional effort since the firing furnaces are typically configured as hood or top hat furnaces in which the electrical resistance heating is provided in the hood thereof whereas the bottom of the firing furnace is free from electrical connections. Also for safety reasons it is not surprising that a furnace of this kind has not made its way because the provision of additional heating elements in the floor of the firing space also requires that an absolutely safe muffling or casing of the heating element at this position must be carried out which muffling in turn obstructs the heat transfer.

Typically, the firing space floor is strongly polluted by deposits that burn into the floor. Therefore, intensive detergents to ensure the cleaning of the floor also require the use of moisture or wetness such as water. With a furnace having a refractory or fire-proof ceramic plate it is acceptable to place it under water, this however not being the case if electrical connections are located thereunder.

In this respect, the existing course of events in dental laboratories must be changed, and an additional special provision for furnaces of this kind must be put into practice.

The reference mentioned above indeed suggests the use of an insulation plate for the floor of the firing space. This, however, is unfavorable for thermal reasons since the heat transfer from the lower heating element into the firing space is impaired by this.

SUMMARY

In contrast to that, the invention is based on the object to provide a firing or press furnace for dental restoration parts according to the claims, which are incorporated by reference herein.

According to the invention it is provided that the floor of the firing space of the inventive dental firing or press furnace is equipped with a heat-conducting element that comprises a comparatively large thermal conductivity. It can amount to 100 W/mk but also 150 W/mK, 200 W/mK or even 250 W/mK.

The heat-conducting element preferably comprises a round construction, i.e., in the top view it is of circular or elliptical shape, but it is in no way limited to this shape, and may be any shape suitable for the furnace, including but not limited to, hexagonal or octagonal shape with rounded corners. The thickness of the heat-conducting element is considerably smaller than its diameter and preferably amounts to approximately one fifteenth part of the diameter, with the basic thickness range amounting to between half the diameter and a hundredth part of the diameter, and the preferred thickness range being between a fifth and a thirtieth part of the diameter.

The shape is here referred to as disk shape, which, however, does not preclude that protrusions and/or recesses for receiving the heat-conducting element are provided in the floor of the firing space on the one hand, and for receiving a press muffle or dental moldings on the heat-conducting element on the other hand.

According to the invention these deviations in shape from a flat shape do not prevent the good heat transfer to the heat-conducting element, or away from the heat-conducting element. The heat transfer to the heat-conducting element predominantly takes place through radiant heat radiating from the heating means of the furnace.

According to the invention it is favorable to provide a dental firing or press furnace for the production of at least one dental restoration part with a firing chamber that is heatable by a resistance heating and comprises a heat-conducting element having a specific thermal conductivity of at least 100 W/mK, the firing chamber being surrounded by a furnace hood upwards and to the sides, and a bottom of the firing chamber extending below the firing chamber as a part of a furnace bottom part, with said furnace hood being capable of being lifted off the furnace bottom part, and with the resistance heating being arranged exclusively in the area of a side wall of the firing chamber and with the heat-conducting element being arranged on the floor or bottom of the firing chamber.

A key to the inventive solution is the insertion of a resistance heating component into a furnace hood, said resistance heating component being arranged in a side wall of the furnace, as well as the attachment of a heat-conducting element that is arranged on the floor or bottom of the firing chamber. With the aid of said heat-conducting element that is thermally coupled with the resistance heating via an annular gap, a notably homogenized temperature distribution in the firing chamber of the dental firing or press furnace is achieved, as becomes apparent in FIG. 5. This improved temperature distribution enables a quality improvement independent of different sizes of dental restoration parts.

According to the invention heat is transmitted across the annular gap and partially via radiant heat to the inventive heat-conducting element from the side but also slanted from above and in this way an independent positioning of the dental restoration parts on the heat-conducting elements is achieved. Surprisingly, in contrast to the usual assumption that hot air rises to the top and that therefore the hottest area is rather at the top, an exceptionally good bottom heat ("hot foot") is achieved.

According to the invention it is nevertheless not precluded, however, that a heat transfer takes place between the heating device and the heat-conducting element through a convection and/or a heat conduction, that is to say a thermal contact. It is also possible to mount a special heat transfer element for improving the thermal coupling, whose purpose is to improve the heat transfer from the heating device to the heat-conducting element. The element could then have the shape of a circular ring and could either be attached to the hood or cover of the furnace or to the heat-conducting element itself, and it can consist of a material that has the same good heat conductivity as the heat-conducting element.

According to the invention it is particularly favorable that an electrical heater is simulated in the floor of the firing space without the need for electrical heating elements at this position. Hereby, the inventive furnace is short-circuit-proof, even if its firing space floor is wiped with a wet cloth as usual. Surprisingly, the cycle time is notedly shorter since a heating or warming of the press muffle or the dental restoration part from below is considerably more favorable than a mere heating or warming from the side, as it is common practice with top hat furnaces or hood kilns, and is additionally provided in the firing or press furnace according to the invention.

The hot heat-conducting element transfers its thermal energy notably more efficient to the press muffle or the dental restoration part. This is not only due to the fact that convection heat flows upwards, but in particular is due to the fact that a direct thermal contact takes place. According to the invention the heat conducting element is substantially closer to the inventive furnace hood or cover than the press muffle or the dental restoration part, because the diameter is larger than for example the press muffle diameter. Due to the typical pivoting of the furnace hood or cover when it is removed, it is not possible to produce the press muffle large enough so that it fills up the entire firing space. Moreover, different press muffle sizes must be used for dental restoration parts of different sizes, which means that also quite small press muffles must be used in a furnace having a firing space diameter of for example three times the press muffle diameter. The heat transfer to press muffles of this kind, up to now merely took place with the aid of radiant heat from the heating coils of the resistance heating laterally attached thereto.

According to the invention heating coils of the resistance heating of this kind are also provided. The lowest spiral coil of the heating coil, however, is disposed quite closely adjacent to the heat-conducting element so that a major part of the heat emitted there is transferred thereto.

Preferably, the inventive heat-conducting element is made of silicon carbide and is of dark or even black color. It absorbs the impinging thermal radiation particularly well compared to the typically used insulation materials, fireclays or ceramic components made of $Al_2O_3$ or similar materials that are employed in the floor area of the dental furnace and that are typically white in contrast to SiC. The same is true for the firing trays used for holding the dental restoration parts made of cordierite or for the press muffles consisting of hard plaster.

Because of the fact that the inventive heat-conducting element, as has been explained before, is flat, it is also possible to refit or upgrade existing furnaces therewith in order to improve the cycle time. Many furnaces have a separate and removable base plate that consists of the same insulation material or fireclay that is used for the temperature insulation in the furnace, because the floor of the dental firing furnace is exposed to high mechanical stresses and is easily soiled, too. The base plate can as well be replaced by the inventive heat-conducting element.

In order to improve the heat transfer between the heat-conducting element on the one hand, and the dental restoration part or the press muffle in which the dental restoration part is to be produced, on the other hand, and also in order to ensure that the dental restoration part and the press muffle are properly centered, the heat-conducting element can be provided with a recess that is custom-fit for the press muffle, i.e., with a recess or notch that surrounds the press muffle, and also provides for a heat transfer along the side walls of the recess through direct contact with the side wall of the press muffle. In the floor of the press furnace as well, a corresponding recess may be provided in which the heat-conducting element is centrally arranged. This also serves to ensure a secure footing of the objects placed therein.

According to the invention it is particularly favorable that the heat-conducting element can remain in the hot firing furnace when the press muffle or the dental restoration part is completed. Insofar as the heat-conducting element has been cooled down by inserting the press muffle, it then adopts again the temperature of the furnace interior during firing interruptions and immediately is available again for the direct and yet uniform but quick heating of the dental restoration part or of the press muffle.

According to the invention, this measure leads to a clear reduction of the temperature gradient during the firing or pressing cycle in the working area, or the firing and pressing cycle time can be shortened at uniform temperature gradients. It is to be understood that it is favorable if the press muffle or the dental restoration part have a large-area contact, for example over several square centimeters, with the heat-conducting element. The heat transfer by means of heat conduction then is particularly good.

Typically, the heat transfer via heat conduction of solid bodies is clearly improved compared to the heat transfer via convection or radiation.

It is particularly favorable if the heat-conducting element extends to the wall of the firing space thereby forming a gap of limited size, i.e., there is no contact between the heat-conducting element and the wall of the firing space. The wall of the firing space is incorporated into the furnace hood, and the furnace hood is typically movable relative to the floor or bottom of the firing space which is formed on the furnace lower part. In this way, the furnace hood may be moved in any desired manner with respect to the floor of the firing space and the heat-conducting element, even if the heat-conducting element clearly expands due to the heating operation. Since next to the lower end of the furnace hood the lowest coil or winding of the heating coil of the heating device is located, an especially good heat transfer takes place across the gap to the heat-conducting element.

It is to be understood that the exact configuration of the gap and the relative dimensions between the furnace hood at its lower edge on the one hand, and the heat-conducting element on the other hand can be adapted to the requirements in large areas. For example, the heat-conducting element can be somewhat increased at the periphery thereof in order to enable a still further improved heat absorption, or in order to indicate and limit the working area for the adjustment of dental restoration parts.

According to the invention it is particularly favorable if an electrical resistance heating or some other thermal heating is used as a heating device since surfaces can be realized in this manner that uniformly radiate the heat. However, limitations exist, since in particular at those places at which the material loading takes place, i.e. at which access to the furnace takes place, a separation of the dental furnace into an upper part and a lower part exists. If several surfaces are to be heated, this means the incorporation of several heating elements that may be connected separately, and thus an additional technical effort and at the same time increased costs.

It is known that the heat transfer via radiation disproportionately increases at temperatures higher than 600° C. compared to the heat conduction. Said heat radiation, however, is eliminated in the direction of the floor of the furnace on which firing trays or press muffles are placed by exactly the inserted firing trays or press muffles. The heating and warming-up of the floor plate if it is constructed from the usual insulating materials or ceramic materials, in this manner is drastically reduced or prevented, respectively.

According to the invention it is now very advantageous that the protruding surface of the heat-conducting element nevertheless is able to readily absorb the still arriving heat radiation and due to its very high heat conduction can quickly and easily transfer the heat radiation below the inserted firing tray in a firing furnace or the inserted press muffle in a press furnace.

In this connection it is also essential that the temperature gradient within the firing space, but especially at the inserted object, is lower in this manner according to the invention. According to the invention the uniform heating of the dental restoration part is substantially co-determined by the heat-conducting element. In this respect, the heat-conducting element is an indirect heating device. It produces a thermal curtain and a uniform thermal distribution, both in the vertical and radial direction of the firing space. This means that the isotherms that represent the temperature distribution within the firing space, are substantially further spaced apart from each other due to the invention, or if regarded the other way around, the temperature gradients or the temperature gradient within the firing space is substantially smaller.

According to the invention it is particularly favorable that the heat-conducting element contributes to the temperature homogenization both in the radial direction and the vertical direction as a result thereof. Since the temperature gradient in the heated furnace, i.e., in the normal operation of subsequent firing cycles, according to the invention is preferably less than 5 degrees within the heat-conducting element, it is also favorable that also in the heat-up phase, i.e. if the furnace that initially is at room temperature, is heated up to the firing temperature of 1200° C. for example, the temperature difference within the heat-conducting element is less than 20 degrees. Surprisingly, hot zones and cold zones may either be fully avoided in this manner, or the tendency to form such zones is clearly reduced.

According to the invention it is particularly favorable if a body made from silicon carbide is used for the heat-conducting element. Pure silicon carbide has a heat conductivity of about 350 W/mk, but also heat conductivities of just under 150 W/mK that are achievable with technical silicon carbide acting in a favorable manner according to the invention. The heat-conducting element may either be realized as a compact compression-molded body or it may comprise any other suitable, principally flat construction. A disk shape can also be implemented for example, if the heat-conducting element is not built up in a solid or compact manner. For example, it may be built in several parts from radial "pieces of cake" or from disks placed on top of each other.

According to the invention the heat-conducting body due to its own high thermal conductivity is particularly resistant to temperature shock, it can be removed and can be cleaned separately. In this connection, it can be favorable that in particular silicon carbide has a very high hardness and for this reason represents a component that may be subjected to very high mechanical stress. This enables for example even a cleaning by sand blasting in order to easily remove highly adhesive fouling and without residue. This is unthinkable for ceramic components usually used, in particular if they are made from the same material as it is used for the insulation material of the firing space.

However, it is also possible, in particular with firing furnaces, to provide a separate firing tray that is placed on the inventive heat-conducting element and on which the dental restoration materials to be burned are placed. The firing tray can consist of any material suitable for this purpose, for example of silicon carbide as well, so that a temperature homogenization with respect to the good thermal conductivity of this material is produced, too, or for example of cordierite or SiNi. Preferably, the mass of said carrier or firing tray compared to the heat-conducting body should be small, in order to optimally exploit the advantage of the heat-conducting body. The carrier or firing tray itself then only functions as a transfer system for loading and unloading the dental furnace.

According to the invention it is particularly favorably provided that the heat-conducting body forms a footprint on its upper side, and as a carrier supports at least a restoration part, a firing tray with at least one restoration part or a press muffle.

According to the invention it is particularly favorably provided that the heat-conducting element is substantially formed in a disk-shaped manner, in particular in a circular disk-shaped manner, and radially projects past or extends past the restoration part or the press muffle.

According to the invention it is particularly favorably provided that the heat-conducting element is spaced apart from the side wall of the firing space thereby forming a gap whose width in particular is less than one third and particularly preferred is one fourth to one twentieth of its diameter.

According to the invention it is particularly favorably provided that the heat-conducting element is centrally located on the floor of the firing space and comprises an edge or rim which between it and a circumferential side wall of the firing space a gap exists as an annular gap whose width remains constant throughout its run.

According to the invention it is particularly favorably provided that the heat-conducting element comprises a height of one twentieth to one third, in particular approximately one tenth of its diameter.

According to the invention it is particularly favorably provided that the heat-conducting element consists of silicon carbide SiC, aluminum nitride AlN or molybdenum.

According to the invention it is particularly favorably provided that the floor of the firing space comprises a thermal insulation material and in particular fireclay.

According to the invention it is particularly favorably provided that the floor comprises a central recess, in which the heat-conducting element is accommodated, in particular in a partially ground-recessed manner.

According to the invention it is particularly favorably provided that the heating device is arranged, in particular, exclusively in the region of the side wall of the firing space and that the floor of the firing chamber is free from a heating device.

According to the invention it is particularly favorably provided that the heat-conducting element is shaped as an alveolar or honeycombed carrier.

According to the invention it is particularly favorably provided that the honeycombs of the alveolar or honeycombed carrier are shaped according to the type of a square pipe that extends vertically, and that the heat-conducting element is formed into lattice shape in the plan or top view.

According to the invention it is particularly favorably provided that prior to the heat treatment process in the firing space, preferably on the floor thereof, a heat-conducting element having a specific thermal conductivity of at least 100 W/mK, is introduced and that a heat treatment cycle for the production of the dental restoration part is started if the firing space and the heat-conducting element have reached a preset operating or stand-by temperature, i.e., a start temperature.

According to the invention it is particularly favorably provided that the heat-conducting element is placed on the floor of the firing space of a conventional dental firing or press furnace and that the press muffle is then placed on top of the heat-conducting element before the firing and/or press cycle takes place.

According to the invention it is particularly favorably provided that a material is used for the heat-conducting element that is harder than the bottom or base part of the dental firing or press furnace.

BRIEF DESCRIPTION OF THE DRAWINGS

Further advantages, details and features emerge from the following description of several exemplary embodiments of the invention in conjunction with the drawings, in which.

DETAILED DESCRIPTION

Figure 1:
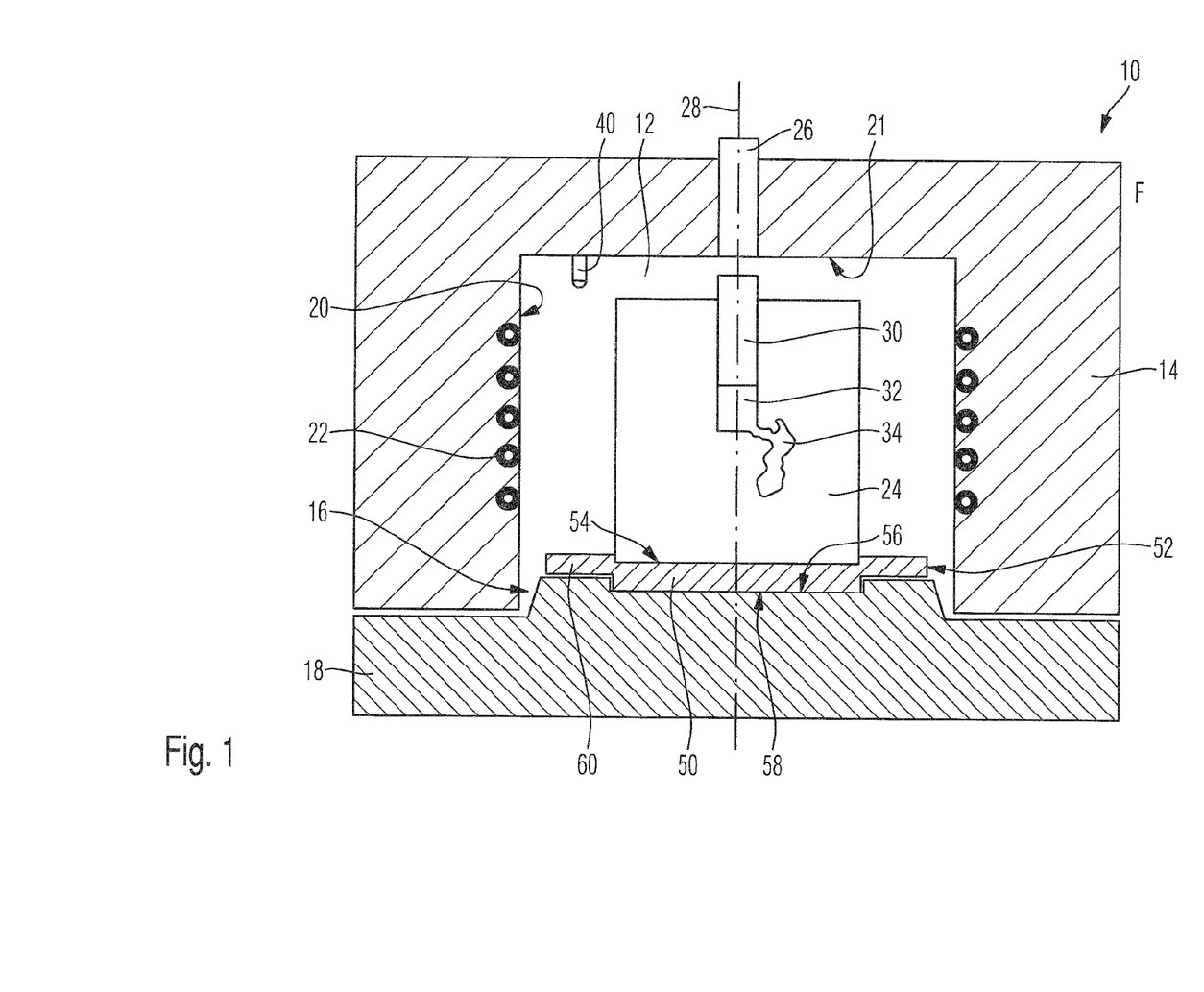
FIG. 1 illustrates a schematic sectional view of an inventive dental press furnace in one embodiment.

FIG. 1 schematically illustrates a dental furnace 10. The furnace 10 comprises a firing space 12 that is surrounded by a furnace hood 14 upward and laterally. A floor or bottom 16 of the firing space 12 extends below the firing space as part of a furnace base 18.

In a manner known per se, the furnace hood 14 is removable from the furnace base 18 with a pivotable support of the furnace hood 14 having worked well.

The furnace hood 14 and the furnace base 18 for the most part consist of a heat-insulating material such as fireclay.

A heating device 22 is provided that annularly surrounds one side wall 20 of the firing space 12.

The heating device 22 is configured as a thermal heating, preferably as a resistance heating device. Basically it is to be understood that any other thermal heating device can be used instead.

In the illustrated exemplary embodiment, the heating device comprises spiral coils of a resistance wire that lie on top of each other in a manner known per se and that rest in corridors (not shown) that are open toward the firing space and substantially extend over the entire height of the firing space or, as it is illustrated here, over little more than half of the firing space.

Even if in FIG. 1, 5 spiral coils are illustrated, it is to be understood that any other suitable number of spiral coils is also possible instead, and for example, a sixth spiral coil can be provided in the embodiment below the lowest spiral coil illustrated in FIG. 1.

The heat radiation emitted by the heating device 22 serves to heat up the firing space 12 in order to be able to form a dental restoration part. To this end, a press muffle 24 is provided that is centrally arranged within the firing space 12, and in fact with a clear distance to the side wall 20 of the firing space. Compared to the diameter of the firing space, the press muffle 24 takes up about half of the inner space of the firing space. A distance or clearance in this respect must always be guaranteed since due to the pivoting movement when opening the hood 14 there would be otherwise the danger that the press muffle 24 is carried away by the hood 14.

In a manner known per se, the upper wall of the hood 14 comprises a recess or aperture. A press plunger 26 is guided within the recess or aperture, said press plunger being vertically movable and extending in the axis 28 of the firing space. The press plunger 26 is destined for pressing on a blank or green body made from dental material. To this end, the press muffle 24 comprises a cylindrical pre-press channel 32. Via a small connecting channel, the pre-press channel is in connection with a cavity or molding area 34 whose shape according to the type of a die or mold determines the later form or shape of the dental restoration part.

During the operation of the dental press furnace 10, the press plunger 26 is at first lowered after the press muffle 24 with the blank 30 has been inserted, so that the pre-press channel 32 as well is completely filled up by the blank 30. Then it is waited until the temperature of the blank 30 and the press muffle 24 has adjusted to the temperature within the firing space 12, so that the dental material becomes liquid or at least viscous. Then a pressure is exerted on the press plunger 26 from above and the plunger transfers the pressure to the blank 30. After having liquified or melted, the dental material of the blank 30 enters into the connecting channel and then into the mold or cavity 34 until it is completely filled up. It is to be understood that instead of the single mold or cavity 34 illustrated here, a plurality of molds or cavities can be provided at radially different positions of the press muffle 24 that are connected with the pre-press channel 32 via separate connecting channels, respectively.

In order to minimize the delay until the dental material has softened, the press muffle 24 prior to the actual press operation is usually heated to a pre-heat temperature in a so-called pre-heat furnace, for example to a temperature of 850° C. The rated temperature within the firing space 12 strongly depends on the dental material that is used and that is to be processed, and on the mass of the press muffle used. For example, while with leucite ceramics a temperature of 1070° C. is required, the firing temperature of lithium disilicate is substantially lower. The temperature and also the temperature profile are detected by means of a temperature sensor 40, and in addition the pressing force of the press plunger 26 and also the movement of the press plunger 26 during the pressing operation are detected and controlled.

The press muffle 24 typically consists of hard plaster or plaster-like compounds in order to ensure the required contour accuracy also in case of a strong rise in temperature. In order to improve the heat absorption it has also been proposed to add color pigments to the compound which are to enhance the absorption of the heat radiation of the heating device 22 of the press muffle. However, the contour accuracy suffers here.

In order to remedy this issue, it is inventively provided to offer a heat-conducting element 50 that according to the type of a disk extends along the floor or bottom 16 of the firing space while covering or nearly covering the same, and that is at least adjacent to the lower spiral coil of the heating device 22 at its outer edge 52. "Adjacent" in this connection refers to a distance of only a few centimeters, for example 1 to maximal 3 centimeters, while the distance between the heating device 22 and the outer side of the press muffle may well amount to 3 centimeters or in the case of small press muffles even to substantially more.

Between the outer edge 52 of the heat-conducting element 50 and the side wall 20 of the furnace hood 14 exists a gap of 1 cm for example, with the furnace hood 14 extending beyond the heat-conducting element 50 downward. Accordingly, the floor or bottom 16 of the firing space 12 is lowered at this position and for the rest is raised or elevated.

The heat-conducting element 50 remains within the furnace 10 even with a remote press muffle. Accordingly, it has the rated temperature upon the insertion of the press muffle 24. The heat-conducting body 50 is in contact with the entire lower side of the press muffle 24. The hot heat-conducting element 50 transfers the heat stored therein and transferred thereto to the press muffle 24 from below so that the press muffle 24 heats up substantially faster and a better temperature homogenization takes place than with conventional furnaces without heat-conducting elements 50 located on the floor of the firing space.

In the illustrated embodiment, the heat-conducting body 50 even comprises a bowl-shaped recess into which exactly fits the press muffle 24. This substantially serves to centrally guide the inserted press muffle.

It is to be understood that with different press muffle sizes, additional small adjustment rings can be used as well that are concentrically insertable into the recess 54 of the heat-conducting element 50 so that there is not only always an improved heat transfer between the heat-conducting element 50 and the press muffle 24 but also a centering of the press muffle 24 takes place, and it is ensured that the press plunger 26 exactly aligns with the pre-press channel 32 of the press muffle 24.

In order to ensure the centering, the floor or bottom 16 of the firing space 12 comprises a respective recess 56 into which exactly fits a circular protrusion 58 of the heat-conducting element 50.

Even if the firing space, the press muffle and the heat-conducting element are described as circular elements here, it is to be understood that an elliptical arrangement is possible instead as well, or for example a hexagonal or octagonal arrangement. In the illustrated exemplary embodiment, the heat-conducting element 50 is made of technical silicon carbide and is black. A side flange 60 of the heat-conducting body 50 extends past the press muffle 24 radially outward. This side flange 60 is always subjected to the heat emission of the heating device 22 and transfers the absorbed heat radiation to the heat-conducting element 50 and thus to the press muffle 24.

The heat-conducting element 50 in the illustrated exemplary embodiment comprises a thermal conductivity of 120 W/mK.

Figure 2:
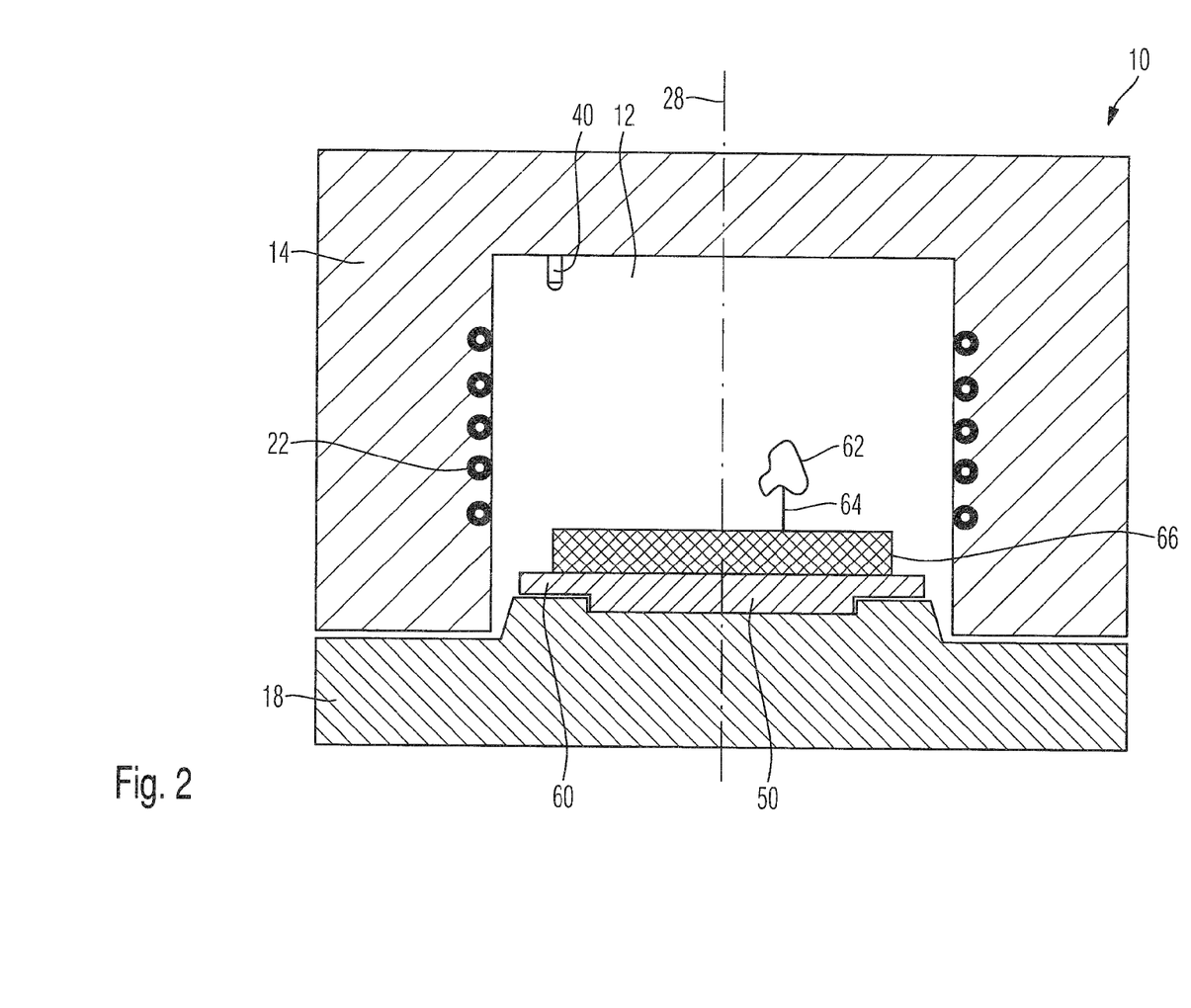
FIG. 2 illustrates a schematic sectional view of an inventive dental firing furnace.

A modified arrangement of a furnace is evident from FIG. 2. The dental firing furnace 10 illustrated here is provided with a furnace hood 14 in a similar manner as it is illustrated in FIG. 1, said furnace hood 14 being pivotably mounted in relation to a lower part 18 of the furnace 10. The same reference numerals here and also in the further figures point out to the same or similar components and do not require any further explanation.

In the embodiment according to FIG. 2 a dental restoration part 62 is fired that is supported on a firing tray 66 via a support rod 64. The firing tray 66 itself with its entire surface rests on the heat-conducting element 50. In this exemplary embodiment, the top side of the heat-conducting element 50 is planar, and the diameter of the firing tray 66 amounts to approximately 80% of the diameter of the firing space 12. In this respect, the diameter of the heat-conducting element 50 amounts to approximately 92% of the diameter of the firing space 12. Also in this case the heat stored in the heat-conducting element 50 and the heat absorbed by the flange 60 is introduced into the firing tray 66 from below so that a heating or warming up of the dental restoration part 62 not only takes place from the sides via the direct heat radiation of the heating device 22 but additionally from below.

Figure 3:
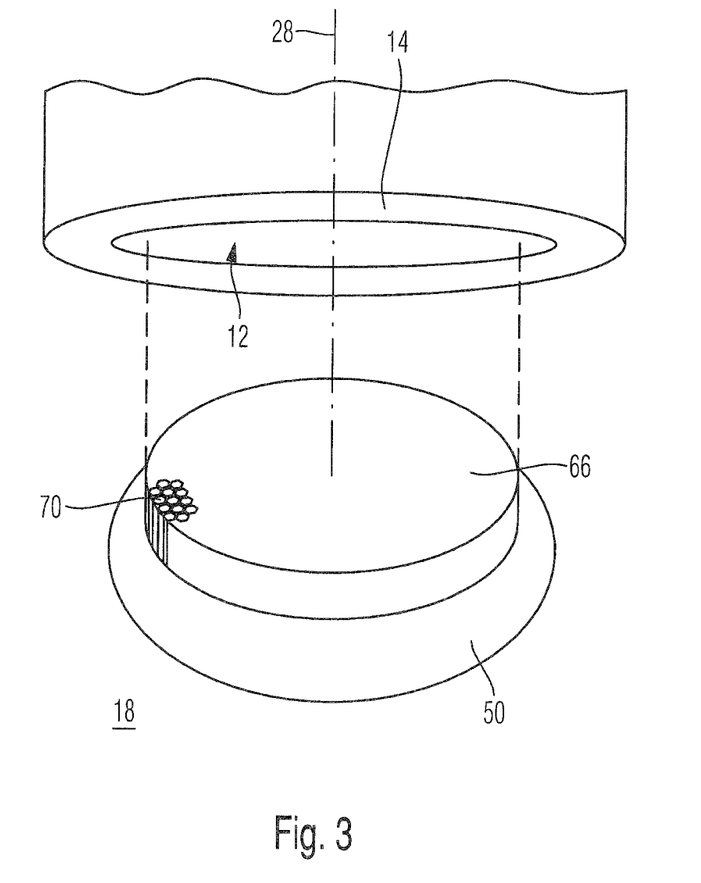
FIG. 3 illustrates a schematic perspective view of a detail of an inventive dental firing furnace.

A possible arrangement of a firing tray 66 is schematically evident from FIG. 3. FIG. 3 moreover illustrates that an inclination between the lower part 18 of the firing furnace and the hood 14 arises due to a lifting of the furnace hood 14. The firing tray 66 comprises a honeycomb or grid structure 70 that is schematically evident from FIG. 3. The honeycombs extend vertically in the illustrated embodiment.

Figure 4:
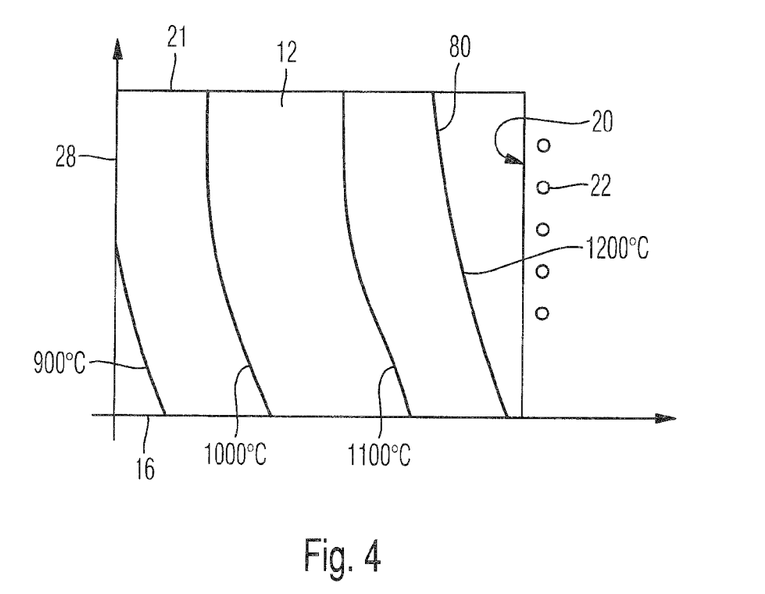
FIG. 4 illustrates the thermal distribution within the firing space of a dental furnace according to the prior art.

FIG. 4 illustrates the course of the isotherms 80 in a conventional furnace. The temperature profile is illustrated along the height of the firing space, i.e. from the floor or bottom 16 to the ceiling wall 21. The horizontal coordinate starts at the axis 28 and ends at the side wall 20 of the firing space. The illustration schematically represents the temperature profile in a quickly heated furnace, into which the press muffle has not yet been inserted.

It is apparent that at the upper external corners, i.e. at the positions where the ceiling wall 21 and the side wall 20 meet, it is at its hottest, i.e. in the illustrated example, the temperature is higher than the 1200° isotherm, while it is coolest at the lower middle part, that is to say at the position at which the axis 28 meets the bottom or floor 16, i.e. it is colder than the 900° isotherm. In this respect, especially during the quick heating operation, a significant temperature gradient exists, and the position adjacent to the dental restoration part that is to be inserted is at its coolest.

Figure 5:
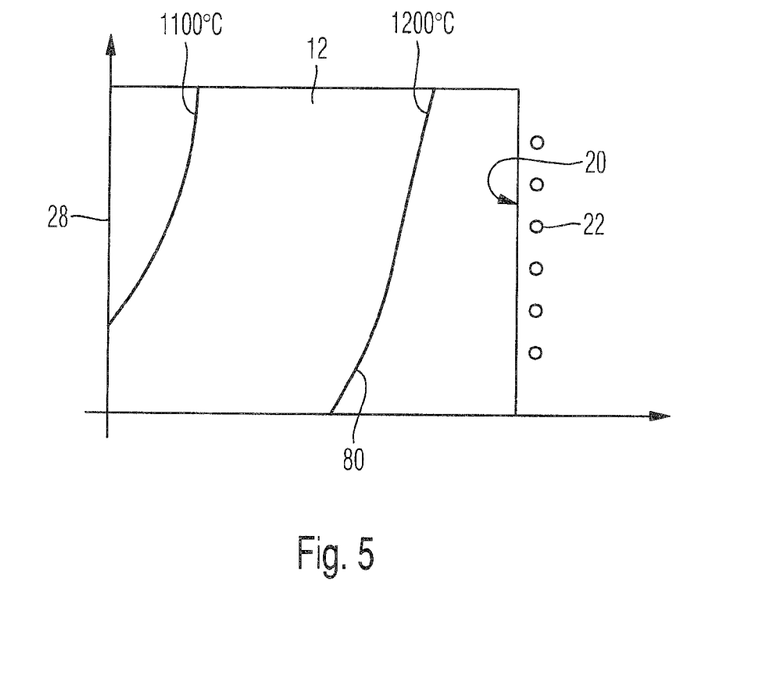
FIG. 5 illustrates the schematic thermal distribution within the firing space of an inventive dental furnace.

FIG. 5 on the other hand inventively illustrates the same temperature profile with the heat-conducting element 50 being inserted. Also in this case, the radial outer part of the firing space 12 is beyond the 1200° isotherm, since at this position the heating device 22 is provided. The heat radiation introduced, however, to a large extent is absorbed by the black and well heat-conducting disk-like plate that forms the heat-conducting element 50. Due to this, it is even somewhat warmer at this position than above the plate or at the upper end of the firing space 12. This finds expression via the opposite inclination of the isotherms compared to FIG. 4 that accordingly extend from the bottom left to the top right, i.e. not from the bottom right to the top left as it is the case in FIG. 4.

Moreover, the distance between the isotherms in the inventive embodiment according to FIG. 5 is substantially larger than it is the case with conventional furnaces according to FIG. 4 which means that a significantly improved temperature homogenization is effected. The position, at which the dental restoration part is introduced later, is approximately located on the 1100° isotherm so that the temperature gradient in the illustrated heated up condition in total is reduced to one third.

Figure 6:
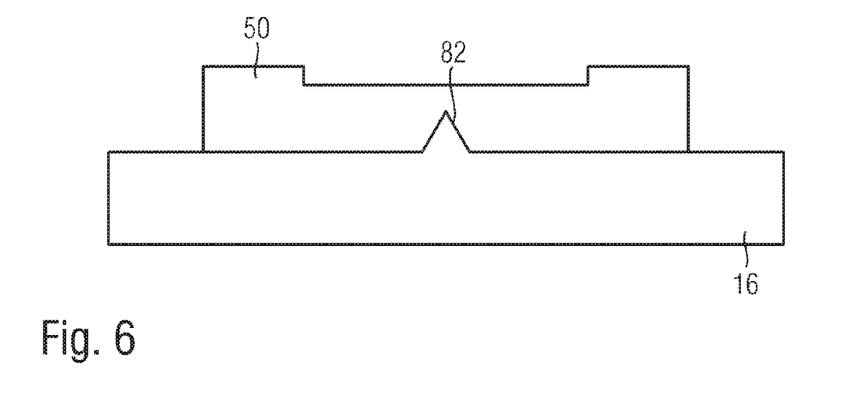
FIG. 6 illustrates a schematic view of a partial section of an inventive dental firing furnace.

Another embodiment of the inventive furnace is shown in FIG. 6. FIG. 6 illustrates in detail just the heat-conducting element 50 and the floor or bottom 16 of the firing space. In this embodiment a cone-shaped element 82 is protruding from the floor or bottom 16 of the firing space which protrudes into a mating recess which is formed in the heat-conducting element 50.

Thus, the correct centering of the heat-conducting element 50 with respect to the floor or bottom 16 of the firing space can also be ensured.

It is to be understood that the cone-shaped centering element 82 need not to be protruding only from the floor or bottom 16 of the firing space but it can alternatively protrude downwardly from the heat-conducting element 50 into a respective mating recess formed in the floor or bottom 16 of the firing space as well. This is not illustrated in the drawings since this alternative represents only the negative form of the embodiment illustrated in FIG. 6.

Figure 7:
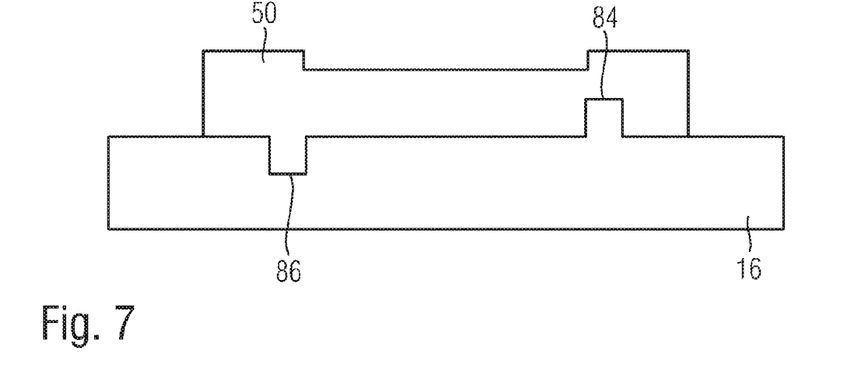
FIG. 7 illustrates a schematic view of a partial section of an inventive dental firing furnace.

In FIG. 7, another embodiment of the inventive furnace is shown. In order to ensure the entering of the heat-conducting element 50 with respect to the floor or bottom 16 of the firing space at least one pin-shaped element is arranged on the floor or bottom 16 of the firing space. It is to be understood that any suitable shape and dimension of an embossment can be chosen instead of said pin which represents a special case of an embossment. In FIG. 7 two pins are shown. First pin 84 which is protruding from the floor or bottom 16 of the firing space into a mating recess in the heat-conducting element 50, and a second pin 86 which alternatively is protruding from the heat-conducting element 50 into a respective mating recess in the floor or bottom 16 of the firing space. It is to be understood that either solely pin 84 or solely pin 86 can be arranged in the center of the floor or bottom 16 of the firing space or the heat-conducting element 50, respectively, or that also any combination of the pins 84 and 86 or even multiple pins similar to the pins 84 and 86 can be arranged in a suitable manner, in order to ensure correct placing and centering of the heat-conducting element 50 with respect to the floor or bottom 16 of the firing space. For the sake of a brief and clear drawing only one pin 84 and one pin 86 are illustrated in FIG. 7.

Figure 8:
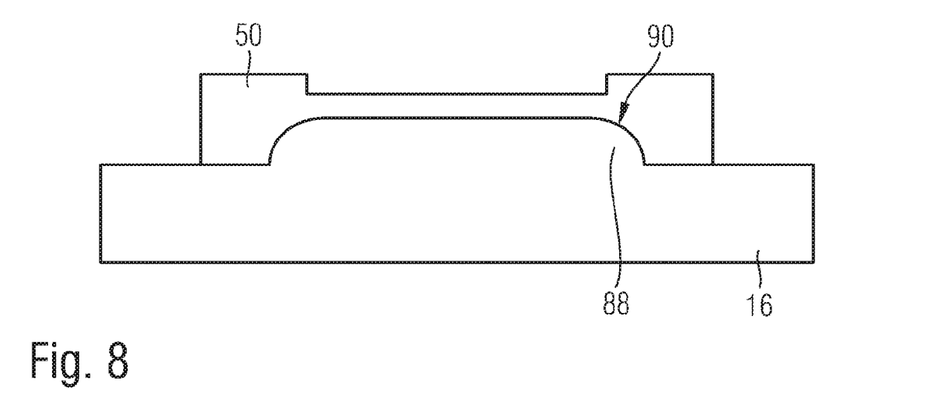
FIG. 8 illustrates a schematic view of a partial section of an inventive dental firing furnace.

Another embodiment is shown in FIG. 8. In order to ensure the centering of the heat-conducting element 50 with respect to the floor or bottom 16 of the firing space the combination of a tongue 88 and a groove 90 can also be employed. Even though a tongue 88 protruding from the floor or bottom 16 of the firing space into a mating groove 90 within the lower surface of the heat-conducting element 50 is shown in FIG. 8 it is to be understood that also the opposite combination—with a tongue protruding downwardly into a groove in the floor or bottom 16 of the firing space can be employed as well. Also, multiple tongue/groove combinations can be used, e.g. arranged in a star-like manner with the tongue/groove combinations pointing to the center of the heat-conducting element 50 and the floor or bottom 16 of the firing space, respectively. Placing the heat-conducting element 50 correctly on the floor or bottom 16 of the firing space can thus be facilitated. Also, alternating arrangement of the upwardly and downwardly protruding tongues can be realized as well.

Figure 9:
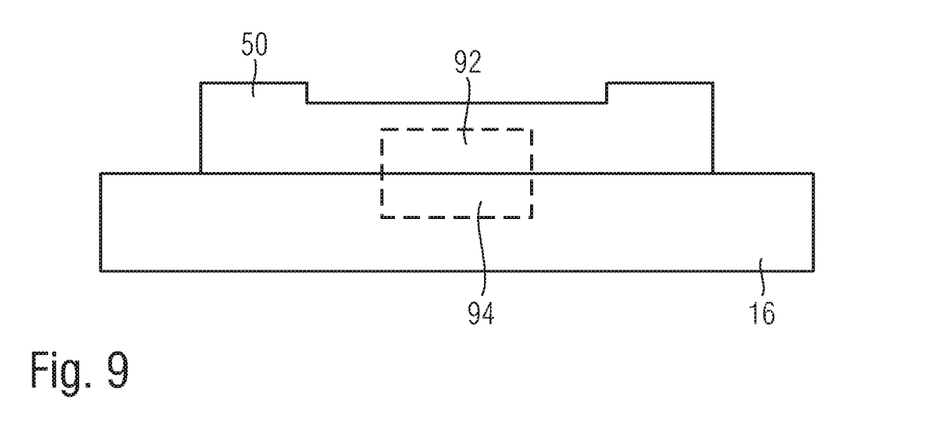
FIG. 9 illustrates a schematic view of a partial section of an inventive dental firing furnace.

FIG. 9 is illustrating a further embodiment of the inventive furnace. In this embodiment instead of a positive locking means magnetic force is employed in order to ensure the centering of the heat-conducting element 50 with respect to the floor or bottom 16 of the firing space. Therefore, in the center of the heat-conducting element 50 and of the floor or bottom 16 of the firing space, respectively, magnetic elements are arranged such that the magnetic part 92 in the center of the heat-conducting element 50 and its counter-part 94 arranged in the center of the floor or bottom 16 of the firing space exert magnetic force to another. The polarity of the magnetic elements must be such that the part 92 and counterpart 94 attract each other. With magnetic elements being capable of exerting a force which is high enough to overcome the friction between the heat-conducting element 50 and the surface of the floor or bottom 16 of the firing space automatic centering thereof can be achieved. It is to be understood that also only one part 92 and counter-part 94 need to be a magnet and the mating part can be made of magnetic metal. In the case of the counterpart 96 being arranged in the center of the floor or bottom 16 of the firing space the magnet can also be an electromagnet instead of a permanent magnet. Any combination of materials and magnetic elements can be used which enables magnetic attraction between the part 94 and counter-part 96.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

The invention claimed is:

1. A dental firing or press furnace for the production of at least one dental restoration part, comprising
a heating device, a firing space that is heatable with the aid of the heating device, a heat-conducting element having a specific thermal conductivity of at least 100 W/mK that is arranged on a floor of the firing space, wherein the floor of the firing space comprises a positive locking element onto which the heat conducting element is accommodated, wherein the heat-conducting element extends along the floor of the firing space while covering or nearly covering the floor of the firing space.

2. The furnace as claimed in claim 1, wherein the positive locking element can be arranged such that the positive locking element protrudes from the floor of the firing space into a mating recess within the heat conducting element.

3. The furnace as claimed in claim 1, wherein the positive locking element protrudes from the heat conducting element into a mating recess within the floor of the firing space.

4. The furnace as claimed in claim 1, wherein the positive locking element comprises at least one pin and/or embossment.

5. The furnace as claimed in claim 1, wherein the positive locking element comprises at least one cone.

6. The furnace as claimed in claim 1, wherein the positive locking element comprises at least a combination of a tongue and groove.

7. The furnace as claimed in claim 1, wherein the heating device comprises a resistance heating device.

8. The furnace as claimed in claim 1, wherein the heat-conducting element forms a footprint on its upper side, and acts as a carrier to support at least a restoration part, a firing tray with at least one restoration part, or a press muffle.

9. The furnace as claimed in claim 3, wherein the heat-conducting element is substantially formed in a disk-shaped manner and radially extends past the restoration part or the press muffle.

10. The furnace as claimed in claim 9, wherein the disk-shaped manner of the heat-conducting element comprises a circular disk-shaped manner.

11. The furnace as claimed in claim 10, wherein the heat-conducting element is spaced apart from the side wall of the firing space thereby forming a gap whose width is less than one third of its diameter.

12. The furnace as claimed in claim 11, wherein the gap is one fourth to one twentieth of its diameter.

13. The furnace as claimed in claim 12, wherein the heat-conducting element is centrally located on the floor of the firing space and comprises an edge or rim, wherein between the edge or rim and a circumferential side wall of the firing space a gap exists as an annular gap whose width remains constant throughout its run.

14. The furnace as claimed in claim 13, wherein the heat-conducting element comprises a height of one twentieth to one third of its diameter.

15. The furnace as claimed in claim 14, wherein the heat-conducting element comprises a height of approximately one tenth of its diameter.

16. The furnace as claimed in claim 15, wherein the heat-conducting element comprises silicon carbide (SiC), aluminum nitride (AlN) or molybdenum.

17. The furnace as claimed in claim 16, wherein the floor of the firing space comprises a thermal insulation material.

18. The furnace as claimed in claim 17, wherein the thermal insulation material comprises fireclay.

19. The furnace as claimed in claim 18, wherein the floor comprises a central recess, in which the heat-conducting element is accommodated in a partially ground-recessed manner.

20. The furnace as claimed in claim 19, wherein the heating device is arranged in a region of the side wall of the firing space and wherein the floor of the firing space is free from the heating device.

21. The furnace as claimed in claim 20, wherein the heat-conducting element is shaped as an alveolar or honeycombed carrier.

22. The furnace as claimed in claim 21, wherein the honeycombs of the alveolar or honeycombed carrier are shaped according to the type of a square pipe that extends vertically, and that the heat-conducting element is formed into lattice shape in the plan or top view.

23. A dental firing or press furnace for the production of at least one dental restoration part comprising
a heating device,
a firing space that is heatable with the aid of the heating device,
a heat-conducting element having a specific thermal conductivity of at least 100 W/mK that is arranged on a floor of the firing space,
wherein the floor of the firing space comprises one part of a centering means and the heat conducting element comprises a mating counter-part of said centering means by means of which the heat conducting element is automatically centered with respect to the floor of the firing space,
wherein the heat-conducting element extends along the floor of the firing space while covering or nearly covering the floor of the firing space.

24. The dental firing or press furnace according to claim 23, wherein the one part of the centering means exerts magnetic force with respect to the counter-part of said centering means.

* * * * *